(12) United States Patent
Digertt

(10) Patent No.: US 11,931,669 B2
(45) Date of Patent: Mar. 19, 2024

(54) CANNABIS EXTRACTION SYSTEM AND METHOD

(71) Applicant: John C. Digertt, Inc., Durham, CT (US)

(72) Inventor: John A. Digertt, Durham, CT (US)

(73) Assignee: John C. Digertt, Inc., Durham, CT (US)

( * ) Notice: Subject to any disclaimer, the term of this patent is extended or adjusted under 35 U.S.C. 154(b) by 70 days.

(21) Appl. No.: 17/313,356

(22) Filed: May 6, 2021

(65) Prior Publication Data

US 2021/0354049 A1     Nov. 18, 2021

Related U.S. Application Data

(60) Provisional application No. 63/024,851, filed on May 14, 2020.

(51) Int. Cl.
    *A61K 36/185*     (2006.01)
    *B01D 11/02*     (2006.01)

(52) U.S. Cl.
CPC ........ *B01D 11/0257* (2013.01); *A61K 36/185* (2013.01); *B01D 11/0207* (2013.01); *B01D 11/0261* (2013.01); *B01D 11/0292* (2013.01); *A61K 2236/13* (2013.01); *A61K 2236/331* (2013.01); *A61K 2236/53* (2013.01)

(58) Field of Classification Search
None
See application file for complete search history.

(56) References Cited

U.S. PATENT DOCUMENTS

| | | | | |
|---|---|---|---|---|
| 6,158,591 A * | 12/2000 | Delp | ............... | B03B 1/00 |
| | | | | 209/172.5 |
| 9,050,631 B2 * | 6/2015 | Raichart | ............... | B07B 1/288 |
| 9,327,210 B1 * | 5/2016 | Jones | ............... | B01D 11/0296 |
| 9,358,259 B2 * | 6/2016 | Hospodor | ............... | B01D 11/0207 |
| 9,926,513 B2 | 3/2018 | Wasserman et al. | | |
| 10,329,513 B2 | 6/2019 | Cumings et al. | | |
| 10,478,747 B2 | 11/2019 | Ko | | |
| 10,626,346 B2 | 4/2020 | Emo | | |
| 10,646,793 B2 | 5/2020 | Ko | | |
| 10,688,410 B2 | 6/2020 | Dimitrelos et al. | | |
| 2018/0078874 A1 | 3/2018 | Thomas | | |
| 2018/0099017 A1 | 4/2018 | Jones | | |
| 2019/0054393 A1 * | 2/2019 | Camilleri | ............... | B01D 11/0257 |
| 2019/0366231 A1 | 12/2019 | Dooley et al. | | |
| 2020/0086229 A1 | 3/2020 | Ko et al. | | |
| 2020/0263109 A1 | 8/2020 | Hansen et al. | | |

FOREIGN PATENT DOCUMENTS

| | | | | |
|---|---|---|---|---|
| CN | 107201454 A | 9/2017 | | |
| WO | 2018215520 A1 | 11/2018 | | |
| WO | WO-2019056126 A1 * | 3/2019 | ......... | B01D 11/0219 |

OTHER PUBLICATIONS

Website document entitled: "Solventless VTS-50" (available at deltaseparations.com/vortex-trichome-separator-bubble-hash-machine). Downloaded Apr. 3, 2023. (Year: 2020).*
Website document entitled: Hashtek Legendary Bundle (A-series deluxe package). Available at evolvedextraction.com/product/hashtek-a-series-50-gallon-lcd). downloaded Apr. 3, 2023. (Year: 2020).*
"IO Extractor—Fully Automated BHO (Butane Hash Oil) Extraction System", Dec. 21, 2020, www.lunatechequipment.com/extraction-equipment, pp. 1-9.
"Families of Resin extraction", Dec. 21, 2020, www.alchimiaweb.com/en/resin-extraction-458, pp. 1-3.

* cited by examiner

*Primary Examiner* — Russell G Fiebig
(74) *Attorney, Agent, or Firm* — Hinckley, Allen & Snyder, LLP; David R. Josephs

(57) ABSTRACT

The system and method of the present invention provides an automated washing and extraction system and method to removed trichomes from cannabis product to create hash resin. Inconsistency is removed from the hash extraction process by automating the washing and extraction cycles thereof. The system and method records the data and tracks all user functions. Manual labor is removed or significantly reduced and time to create the final product is greatly lessened. Thus, more hash can be produced in a shorter amount of time. Moreover, the present invention allows the end user a controlled and accurate and efficient way of producing large quantities of solvent-free hash in a short amount of time while doing so in a consistent, repeatable and cost-effective manner.

12 Claims, 6 Drawing Sheets

CANNABIS EXTRACTION SYSTEM AND METHOD

CROSS REFERENCE TO RELATED APPLICATION

This application is related to, and claims benefit from, U.S. Provisional Application No. 63/024,851, filed on May 14, 2020, entitled "CANNABIS EXTRACTION SYSTEM AND METHOD," incorporated by reference in its entirety, herein.

BACKGROUND OF THE INVENTION

The invention related generally to extraction of cannabinoids from cannabis plant material to make hash and other products from the cannabis plant.

It is well known to extract cannabinoids from cannabis plant material with the assistance of chemical solvents. However, there is serious concern regarding the health issues associated with the use of such chemical solvents for cannabinoid extraction. Besides the increased risk of an explosion in the presence of hazardous materials, the final product could contain a harmful amount of residual solvents. Many government regulations are in place that set cutoff limits for the maximum amount of solvent that can be present in a cannabis product.

Therefore, health-conscious consumers and those using cannabis for medical purposes have turned to solvent-free cannabis extracts to avoid consuming chemical toxins during inhalation. Solvent-free extracts provide customers with a cleaner alternative to solvent-based extracts, such as BHO or $CO_2$ oil.

Cold or ice water extraction of cannabinoids from cannabis plant material is well known in the art for solvent free extraction to address these concerns. It is well known to use ice, water, agitation and filtration to separate the trichomes present on the plant from the raw cannabis material. This process works because the cannabinoids are not water soluble. Moreover, frozen cannabis product is preferably used because the resin gland trichomes can break off from the main plant more easily thereby resulting in a better and complete extraction.

One of the first methods by which hash was extracted without the use of solvents was by hand-rubbing the frozen or cold flower buds and scraping off the sticky trichomes with a knife forming them into a ball. Such a manual method for making solvent free hash is to wash and separate by means of a hand paddle and hand screen. The disadvantages of this method are that it is very inconsistent and very labor intensive. Moreover, replicating the washing and collection process from batch to batch is very difficult to do as well as controlling the temperatures of all vessels. Ice is also needed to keep the product cold and consumes large volumes of ice per batch. Also, the melt rate of ice is difficult to control so, as a result, the temperatures provided by the ice to maintain temperature of the flower buds is very inconsistent. As a result, the end product can be inconsistent in results and in quality.

However, the foregoing solvent-free solutions are not enough and fail to meet the needs of the extraction and processing needs of the modern cannabis industry.

In view of the foregoing, there is a demand for a solvent-free hash extraction system and method of operation thereof.

There is a need for a solvent-free hash extraction system and method that is automated and repeatable.

There is a need for a solvent-free hash extraction system and method that is more efficient that can produce superior solvent-free hash product.

There is a need for a solvent-free hash extraction system and method that extracts trichomes from the cannabis plant in a more consistent and repeatable manner.

There is a need for a solvent-free hash extraction system and method that uses more consistent cold temperatures.

There is a need for a solvent-free hash extraction system and method that is less labor intensive than with previous systems and methods.

SUMMARY OF THE INVENTION

The present invention preserves the advantages of prior art solvent-free hash extraction systems and methods. In addition, it provides new advantages not found in currently available systems and methods and overcomes many disadvantages of such currently available systems and methods.

The system and method of the present invention takes the inconsistency out of the hash extraction process, namely a cold or ice extraction process, by automating the washing and extraction cycles of the hash making operation. The equipment of the system of the present invention also can record the data and track all user functions. By creating a machine that greatly reduces or eliminates the amount of manual labor out of this process, the time to create the final product decreases and thus more hash product can be produced in a shorter amount of time for better production yields.

The object of the present invention is to allow the end user a controlled and accurate and efficient means of producing large quantities of solvent free hash in a short amount of time and being able to do that consistently day to day in a cost-effective manner, also allowing the end user to track his operations and better control his extraction process.

A further object of the present invention is to provide a solvent-free hash extraction system and method that is more efficient that can produce superior solvent-free hash product.

There is a further object of the present invention to provide a solvent-free hash extraction system and method that extracts trichomes from the cannabis plant in a more consistent and repeatable manner.

Yet another object of the present invention is to provide a solvent-free cold/ice hash extraction system and method that uses more consistent cold temperatures.

A further object of the present invention is to provide a solvent-free cold/ice hash extraction system and method that is less labor intensive than with previous systems and methods.

BRIEF DESCRIPTION OF THE DRAWING FIGURES

The novel features which are characteristic of the present invention are set forth in the appended claims. However, the invention's preferred embodiments, together with further objects and attendant advantages, will be best understood by reference to the following detailed description taken in connection with the accompanying drawings in which:

DESCRIPTION OF THE INVENTION

Figure 1:
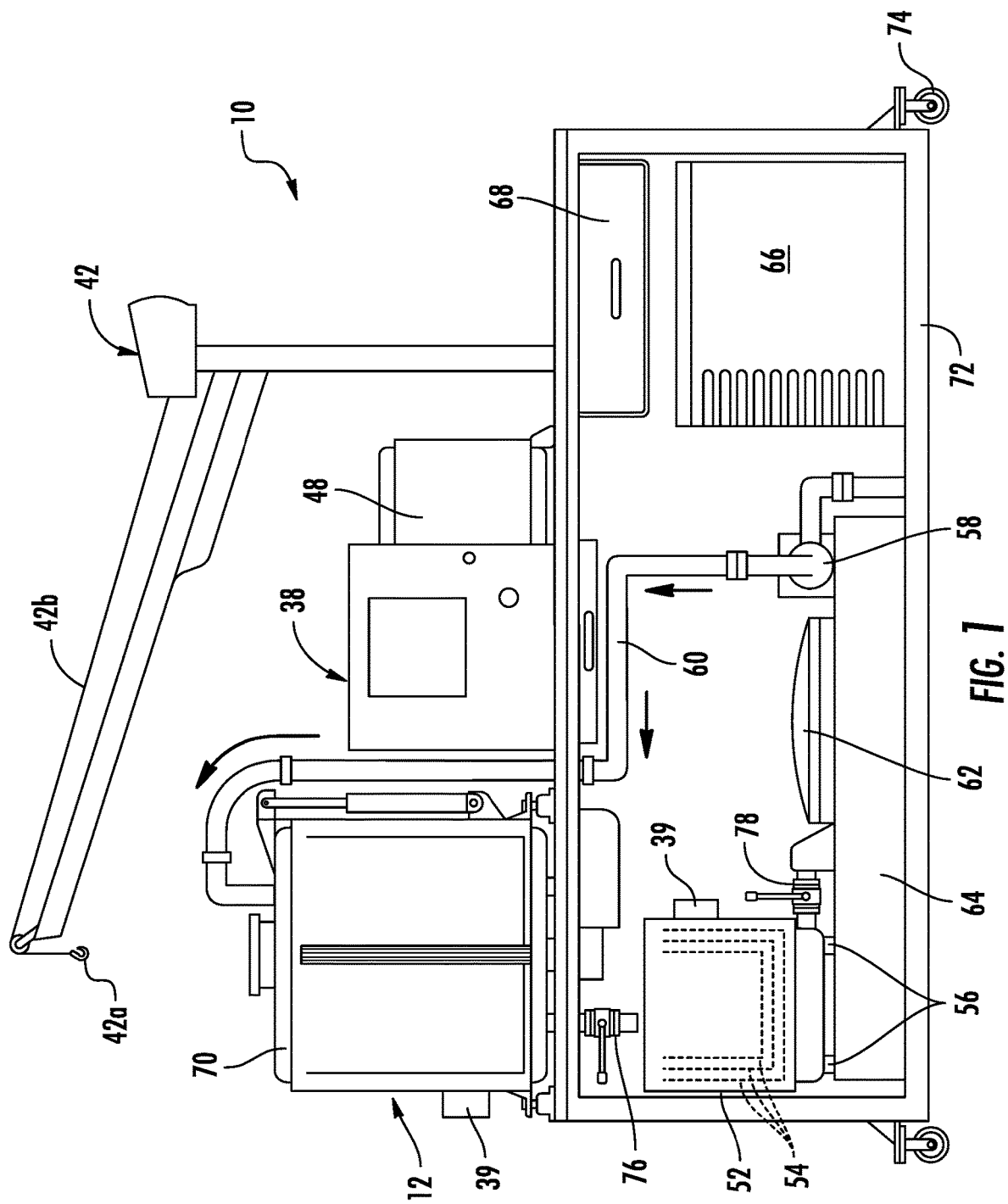
FIG. 1 shows a side partially broken away elevational view of the cannabis extraction system of the present invention.

As can be seen in FIG. 1, a side partially broken away elevational view of the cannabis extraction system 10 of the present invention is shown. The system 10 is a complete hash washing, extraction and collection production plant configured and arranged in an all-in-one system that includes its own chiller and chilled water make up system.

Figure 2A:
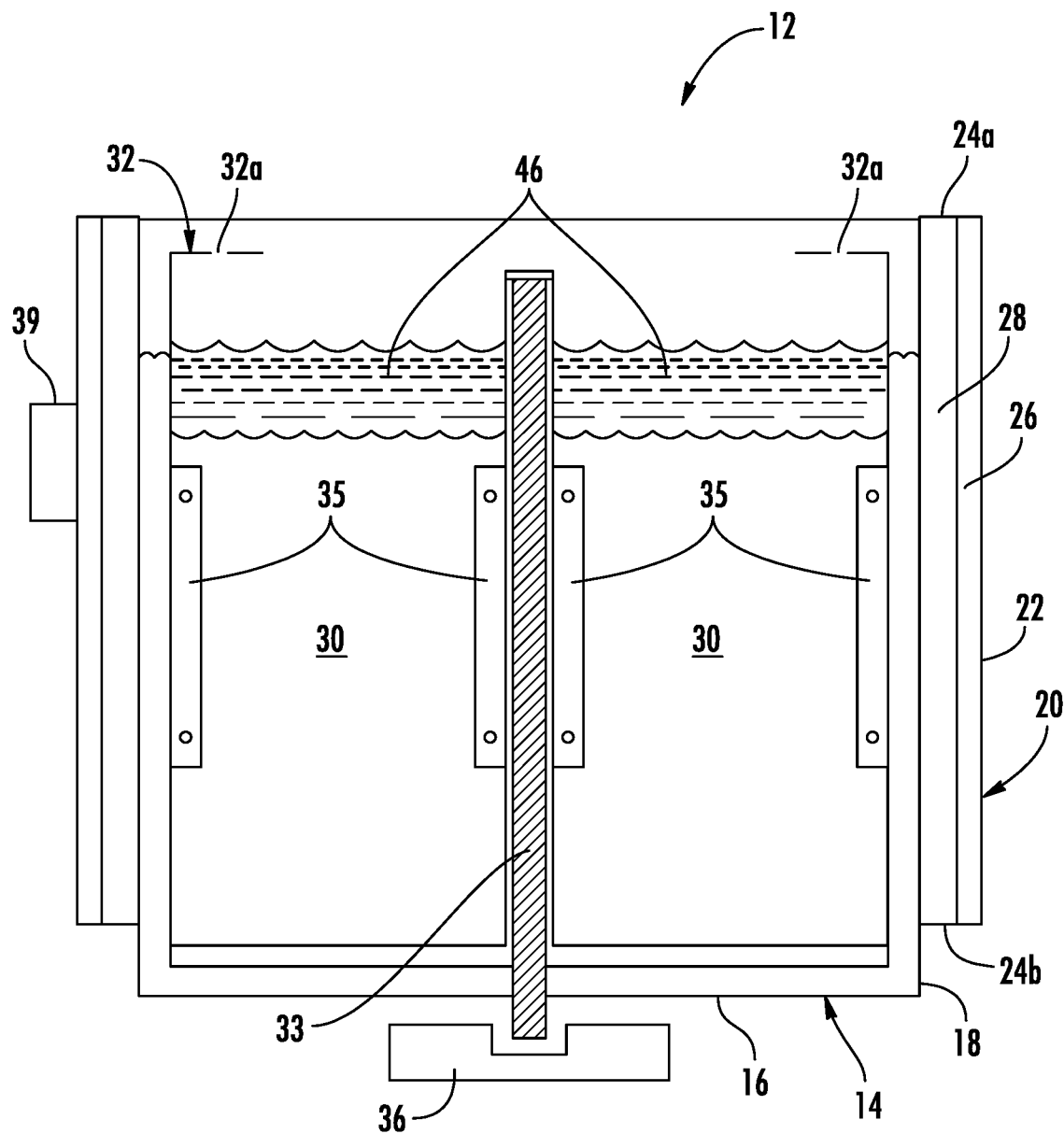
FIGS. 2A and 2B show a partial cross-sectional view of a preferred embodiment of the main extraction vessel used in the system of the present invention.
Figure 2B:
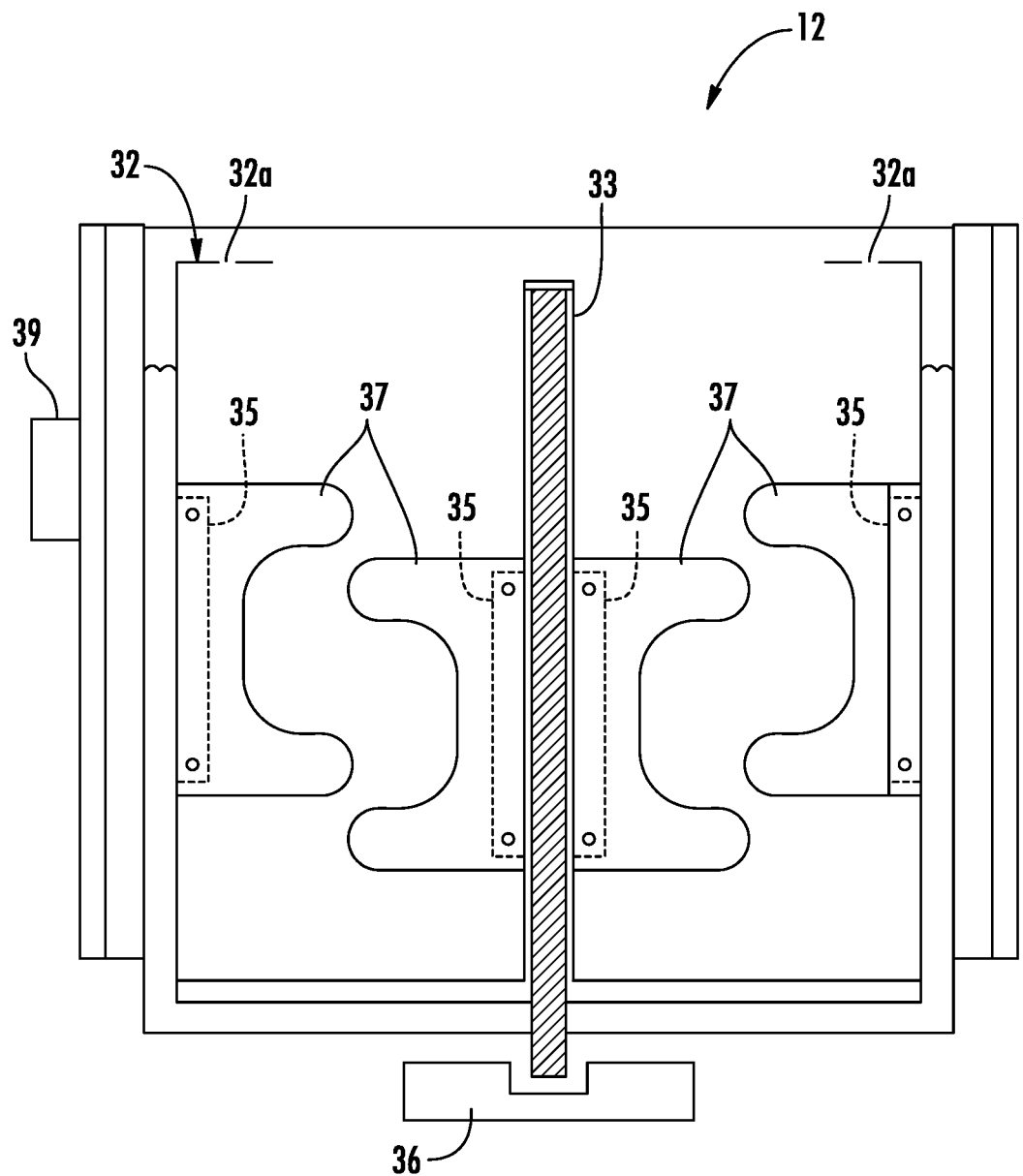
Figure 3:
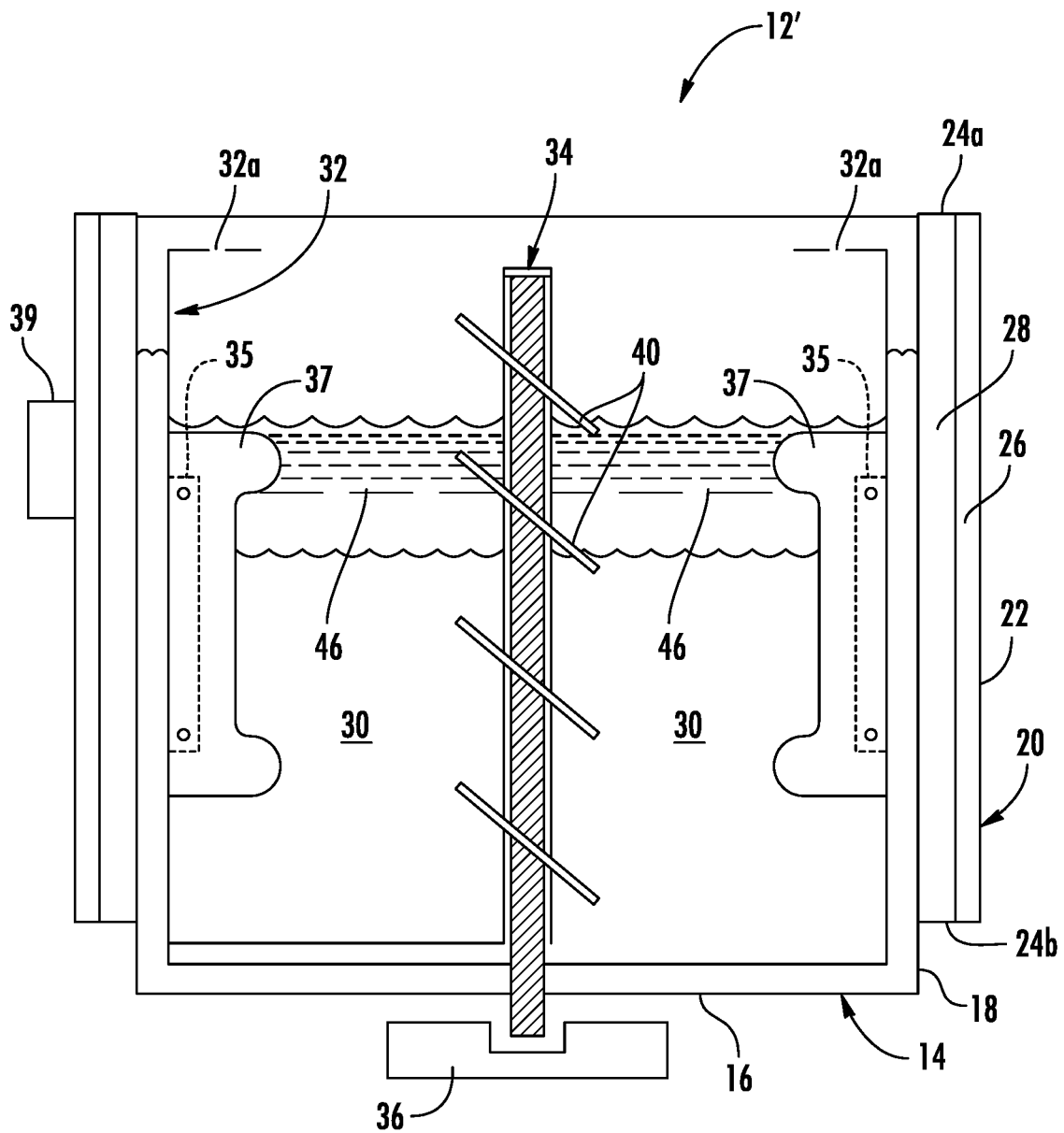
FIG. 3 shows a partial cross-sectional view of an alternative embodiment of the main extraction vessel used in the system of the present invention.

The system 10 of the present invention first includes a preferred embodiment of a main extraction vessel 12 that is preferably a multi-wall tank, such as a triple wall construction. Details of the triple wall construction of the main extraction tank 12 are shown in FIGS. 2A, 2B and 3. The preferred embodiment of the main extraction tank 12 includes an inner tank 14 with a tank bottom 16 and side/outer walls 18. Surrounding the inner tank is a wall construction that includes an exterior tank 20 that preferably has an outer wall 22 that is stainless steel with a brushed finish but may have other finishes, such as a mirror finish. The outer wall 22 includes encapsulating top member 70, as seen in FIG. 1, and bottom flanges 24a, 24b to contain an insulation jacket 26 and an intermediate glycol jacket 28 therein. Preferably, the glycol jacket 28 is positioned adjacent to the inner tank wall 18. Also, the insulation jacket 26 is preferably positioned between the glycol jacket 28 and the stainless steel exterior tank 20. The intermediate jacket 28 is preferably made of glycol but can be other materials. Further the outer insulative jacket 26 is preferably made of closed cell polyurethane foam but can be made of any appropriate insulation material.

It should also be understood that the use of a triple wall construction with a glycol jacket and an insulation jacket is a preferred embodiment of the present invention. However, other configurations of wall construction, such as a double wall or single wall construction, are still contemplated and within the scope of the present invention.

The entire system 10 is preferably configured on a large frame 72 with wheels 74 for ease of transport of the entire system 10.

The multi-wall construction of the present invention therefor provides a defined inner space that can be efficiently chilled via the glycol jacket 28 that interfaces with the outer surface of the inner tank wall 18. The outer insulation jacket 26 is insulated, which allows the inner tank 14, containing the frozen cannabis flower 30, to be chilled more efficiently and consistently.

Still referring to FIGS. 2A, 2B and 3, a removable, preferably stainless steel, washing mesh basket 32 is provided. The removable mesh basket 32 slidably resides inside the inner tank wall of inner tank 14.

FIGS. 2A and 2B show a preferred embodiment of the mesh basket that includes an internal post 33 fixed to the mesh basket 32 so that the post 33 rotates with the mesh basket. As seen in FIG. 2A, a number of internal agitation paddle mounting brackets 35 are fixed to the internal female drive hub and on the interior wall about the periphery of the mesh basket, such as by welding. FIG. 2B shows agitation paddles 37 secured to the mounting brackets, by removable fasteners, such as bolts and the like. The size, shape and configuration of the agitation paddles 37 can be selected to suit the job at hand, the cannabis strain being processed as well as the required processing parameters. For a different job, the paddles 37 may be easily switched out for different paddles. To assist with agitation during soaking and washing, one or more preferably adjustable vibrators 39 may be affixed to the exterior of the main extraction tank 12 to keep product moving and increase separation.

It should be understood that the internal post 33 and basket 32 arrangement may also be rotated and reciprocated using any known drive mechanism, including any gears or linkages interconnected to a motor that interconnected to the control system 38, as shown in FIG. 1, of the present invention and includes an internal 8 female spline coupler/drive hub 36 for driving/rotating the post and basket attached thereto with paddles affixed thereto. This allows for precise control of the rotation, in both directions, of the basket 32, for the soaking and washing steps described in detail below.

In the alternative embodiment 12' of the main extraction tank of FIG. 3, the washing mesh basket 32 includes an integrated auger 34 about an internal 8 female spline coupler/drive hub 36 similar to the drive used in FIGS. 2A and 2B. The auger 34 has a helical "paddle" 40 that is permanently fixed to the mesh basket 32 and rotates therewith. Removable and customizable paddles 37 are also attached to the interior of the outer wall of the mesh basket 32 in similar fashion to the preferred embodiment 12 of the extraction tank of FIGS. 2A and 2B. It should be understood that the auger 34 and basket 32 arrangement may also be rotated and reciprocated using any known drive mechanism, including any gears or linkages interconnected to a motor that interconnected to the control system 38, as shown in FIG. 1, of the present invention for precise control of the rotation of the auger 34 and basket 32 for the soaking and washing steps described in detail below.

The tanks 14, 20 and various components of the cannabis extraction system of the present invention, such as the internal post 33, auger 34, paddles 37 and basket 32, are preferably made of a sanitary material that can be easily and quickly cleaned, such as stainless steel.

At the top of the mesh basket 32, whether it includes a post 33 with paddles 37 removably attached thereto or a fixed auger 34 with helical paddle 40, are a number of basket handles/lifting eyes 32a to facilitate installation into the inner tank 14 as well as removal from the inner tank 14. The system 10 is preferably equipped with a winch 42, such as a 2000 pound power winch, to help install and remove the mesh basket 32, containing cannabis plant matter 30 therein, from the inner tank 14. For example, the mesh basket 32 is preferably lifted by the hook 42a and cable(s) 42b of the winch 42.

As can be understood, the removable basket 32 increases productivity because once a loaded basket 32 has been processed and spent as a result, another basket 32 loaded with new cannabis that is ready for processing can quickly and easily replace the already processed spent basket 32 to cut down on down time. Thus, multiple baskets 32, preloaded with material 30 for processing, can be prepared in advance to speed up processing of multiple batches of material 30. Moreover, the removeable mesh basket 32 also allows for quicker and easier cleaning of the main extraction vessel 12. Also, cleaning of the mesh basket 32 is greatly facilitated when it can be separated from the rest of the system 10 for its own cleaning and then subsequent loading with cannabis material 30 for extraction and collection processing.

Figure 4:
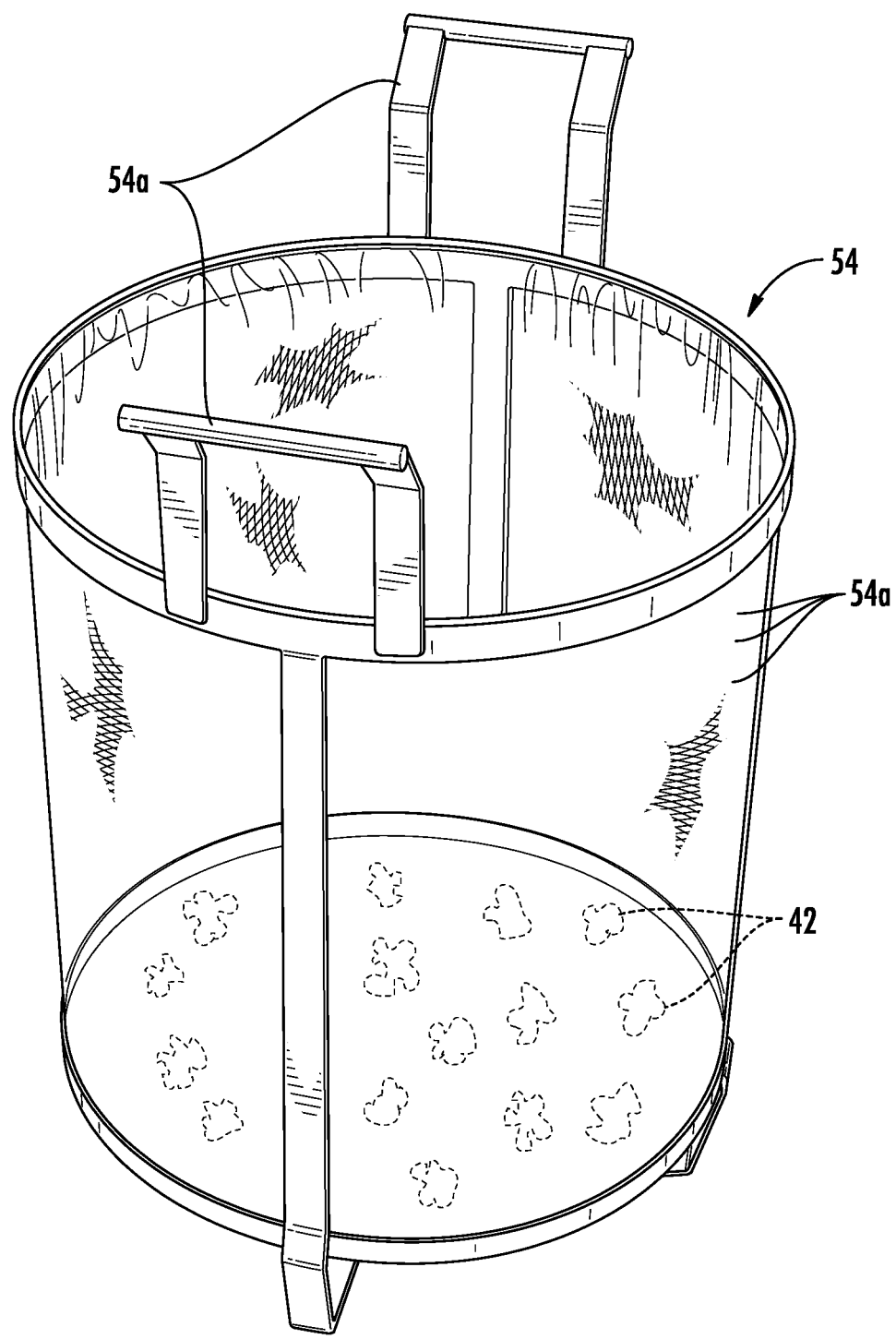
FIG. 4 shows a filtration basket used as part of the separator collection tank.
Figure 5:
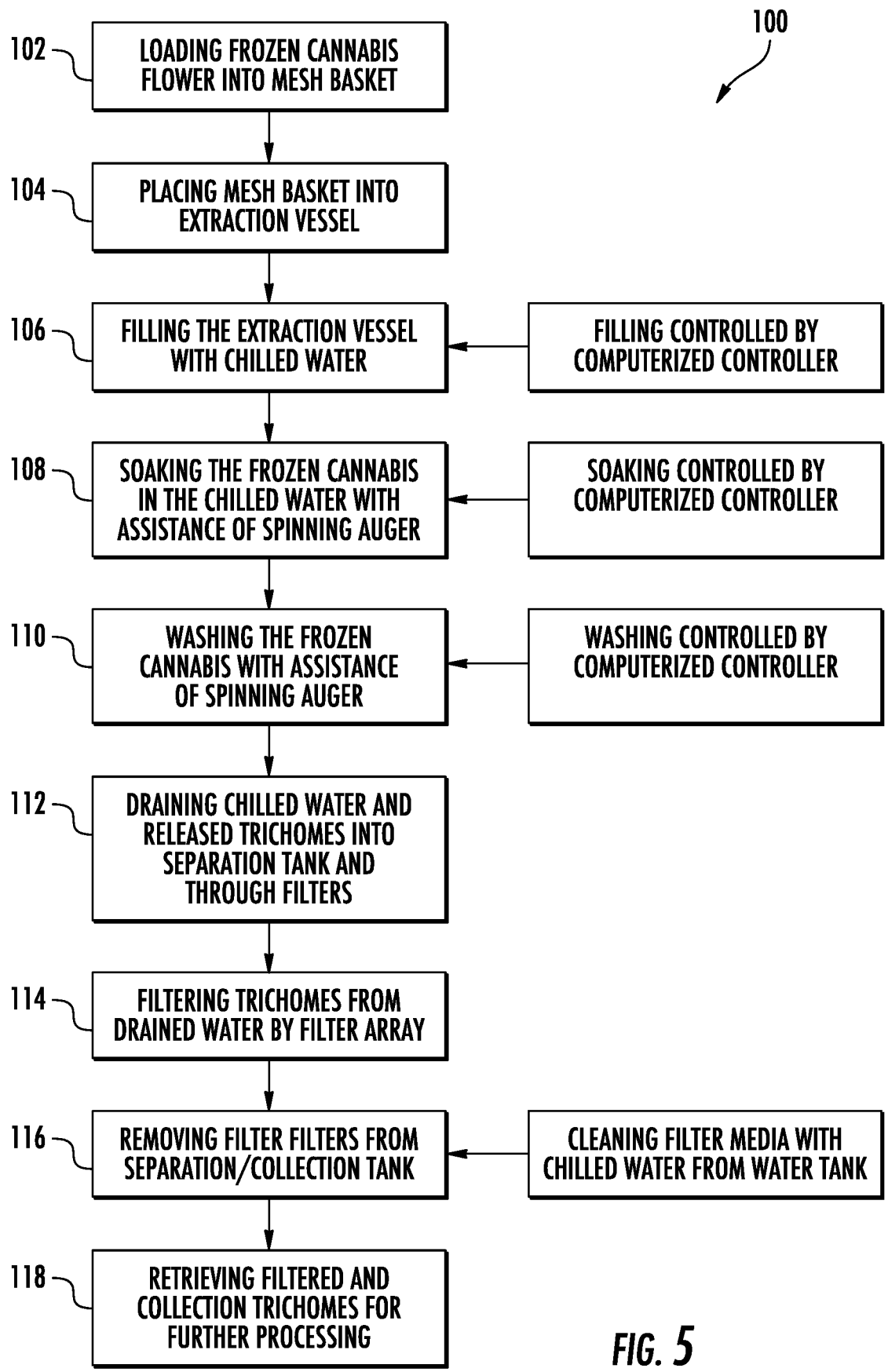
FIG. 5 shows a flow chart illustrating the method of the present invention.

In operation, according to the method 100 of the present invention as can be seen in FIG. 5, the removable mesh basket 32 is first loaded with frozen "raw" cannabis flower material 30 at step 102. It should be understood that the system and method of the present invention greatly facilitates and automates water-based cannabis extraction by use of ice, water, agitation and filtration to separate the trichomes present 42 on the plant from the raw cannabis material 30. This process works because the cannabinoids are not water soluble. Moreover, frozen cannabis product 30 is preferably used because the trichomes 42, as seen in FIG. 4, can break off from the main plant more easily thereby resulting in a better and complete extraction.

For example, as stated above, multiple mesh baskets 32 can be loaded with such material 30 in preparation for processing. The mesh basket 32, loaded with frozen raw cannabis flower material 30, is slid into, and installed into the inner tank 14 to a position of that shown in FIG. 2 and as seen in step 104 of FIG. 5. The extraction vessel 12, with mesh basket 32 and cannabis 30 flow therein and now residing in the inner tank 14, is then filled with water 46, as in step 106 of FIG. 5. More specifically, the main extraction vessel 12, with a loaded basket 32 installed therein, is filled with clean treated and chilled water 46 that comes from a triple wall stainless steel make up water tank 48.

In accordance with the present invention, the system and method are preferably automated and computer controller 38 to facilitate repeatably and accurate operation of the system 10 of the present invention. For example, the present invention includes a main controller 38 for such operator control of the system to carry out the method. More specifically, the operator uses the main controller 38 to instruct the system to fill the main extraction vessel 12 or 12' with an exact amount of water 46 every cycle to allow for exact cycle repetition every time. For example, the computer controller 38 (and control panel associated therewith) can be fully programmed to control speed, time, alternating speed, alternating time, direction in a multi-stage program to customize each step of each cycle. As a further example, the controller 38 can be programmed to allow for multiple "sections" of washing where the wash cycle can be broken down into a beginning, middle and end and have different speeds and directions of rotation and times in each section. The foregoing is fully monitored, recorded and saved for future batches for quality control, efficiency, repeatability and the like. For example, the main controller 38 can monitor and record and provide alerts and alarms for parameters such as high temperatures, low temperatures, high or low water level in storage tanks, glycol temperature, as well as over, high and low speeds, and the like.

Once the main extraction vessel 12 or 12' is loaded with frozen product 30 and the water 46 is introduced, a soaking step 108, in FIG. 5, is ready to be begin. The controller 38 causes the basket 32 and agitation members 37 and/or 40 to slowly begin to spin and alternate direction and give the product 30 time to soak, in a repeatable automated fashion.

The operator can adjust and pre-program the time speeds and direction of all functions in the main controller cabinet 38 to accommodate different types of product 30 that is being processed and to adjust the amount and manner of soaking/washing, as needed for the current job. The programming of the operation, including for soaking and washing, can be saved for easy recall and accurate repetition of the process.

Once the soaking cycle 108 is over, the washing cycle 110, seen in FIG. 5, can begin. The machine washes by rotationally reciprocating the wash basket 32, and paddles 37 in FIGS. 2A and 2B or auger 34 and paddles 40 in FIG. 3, back and forth for a predetermined amount of time, cycle and speed. All of these parameters can be adjusted and preprogrammed to suit the job at hand.

Once the wash cycle is completed and water is drained from main extraction vessel and all trichomes are collected as described below, the spent product that was just washed is preferably spun at high speed in a "dry" cycle to remove water and make the wasted product weigh less and cost less to dispose of as well as mitigate mold growth while waiting to dispose of such spent product. Such drying can also allow the product to be reused in another process, such as being extracted in an ethanol extraction system or butane or C02.

After the desired washing cycle(s) are complete, the operator drains the main extraction vessel 12 as in step 112 of FIG. 5, via output valve 76, into a double wall stainless steel insulated separation/collection tank 52 that is preferably positioned directly below the main extraction vessel 12 or 12'. This is carried out by the assistance of gravity and avoids exposing the extracted product 42 to any mechanical pumps or added heat. The insulated stainless-steel separation/collection tank 52 includes filter media screens, such as a filter basket 54 with handles 54a in FIG. 4, where draining media flow therethrough (containing water 46 and trichomes 42) and then into the separation/collection tank 52 thereby providing a cold collection place. An array of filter media 54 of different pore sizes can be used to carry out the desired filtration, as in step 114 of FIG. 5, to collect the desired cannabis product for later processing. A single filter media basket 54 is shown in FIG. 4, other filter baskets 54 are similar but with different pore size holes 54a therein. Such a graded filtering of trichomes 42 is well known to separate out and collect such trichomes for later drying and processing. The present invention can take advantage and employ such graded multi-stage filtering for optimal collection of trichomes 42.

For example, they system and method of the present invention may use known "bubble bags" (not shown), which are very well known in the art. These bags are typically made of nylon but can be made of other materials. Alternatively, as seen in FIG. 4, a metal drop-in basket filters 54 may be employed instead to replace the mesh bubble bags to provide a more commercial and durable filtration solution compared to nylon sacks or bags. The metal filter baskets 54 are preferably made of stainless-steel but can be other metals or even other materials. In accordance with the present invention, is also envisioned that a mixture of nylon bags and stainless-steel metal basket filters 54 may be employed to suit a given process, cannabis strain or other processing requirement at hand.

Whether nylon bags or metal mesh basket filters 54 are used alone or in combination with each other, multi-stage graded filtration is desired for quality filtration. For example, such stacked filters (whether nylon bags, metal filter baskets 54 or a combination thereof) are preferably used to separate out unwanted debris and different quality trichomes 42 (due to size) from a cold/ice extraction process of the present invention. Preferably, the filters, generally referred to as 54, are stacked/nested form where the largest pore size bag or filter basket 54 is at the top and where the bags or filter baskets 54 have a successively smaller pore size as the water 46 and trichomes 42 travel together downstream/downward with the assistance of gravity. Although not limited to this array, below is an example array of filters 54 with different micron pore sizes that may be used with the system and method of the present invention 10 and what each filter typically collects:

220 micron filter (typically debris being filtered out)
190 micron filter (typically debris being filtered out)
160 micron filter (typically low quality trichomes)
120 micron filter (typically high quality trichomes)
90 micron filter (typically the best quality trichomes)
73 micron filter (typically high quality trichomes)
45 micron filter (typically medium quality trichomes)
25 micron filter (typically low to medium quality trichomes)

To assist with agitation during soaking and washing, one or more preferably adjustable vibrators may be affixed to the exterior of the separation/collection tank to keep product moving and increase separation and improve filtering. This is preferred over the prior process of manually shaking "bubble bags" by hand as it is more reliable, more consistent and much less labor intensive.

After filtration, the nylon bags, metal filter baskets 54, or combination thereof, are individually be slid out and removed from the separation/collection tank 52, as also seen in step 116 of FIG. 5. Then, the trichomes 42 are retrieved from each filter bag or filter basket 54 and then further processed, as seen in step 118 of FIG. 5, such as being placed on drying parchment paper (not shown), and the like.

Therefore, as the water 46 and extracted trichomes 42 pass through the filter screens 54 and then drain into the double wall stainless steel separation/collection tank 52, the cannabis trichomes 42 are collected on the screens. The separation/collection tank 52 is sized to allow an entire cycle of water 46 to collect in it and remain chilled until it is needed for the next cycle. Also, for ease of cleaning the separation/collection tank 52 is positioned on slide-out rails 56 so the operator may gain easy access to the interior of the separation/collection tank 52 and the filter screens 54 therein, particularly for cleaning thereof.

The chilled water makeup tank 48, that was previously used to fill the main extraction vessel 12 with chilled water 46, also provides water 46 for a cleaning operation where the operator carries out a chilled pressurized wash down of the screens 54 in the double wall separation/collection tank 52. Once the screens 54 are washed, the slide out rails 56 under tank 52 facilitates the operator to easily slide out the tank 52 from under the unit, remove the screens 54 and then thoroughly clean this separation/collection tank 52.

As can be understood, once the main extraction vessel 12 or 12' is reloaded with a new mesh basket 32 pre-loaded with frozen product 30 to be processed, the operation and method of the present invention can be started and then carried out again. Several mesh baskets 32 may be pre-loaded with frozen cannabis product 30 in advance to facilitate processing of such several pre-loaded baskets 32 of cannabis flower 30 in rapid succession thereby reducing the overall time of processing.

Moreover, the water 46 in the insulated holding tank 48 can be brought back into the main extraction vessel 12 or 12', if desired, via a sanitary pump 58, via pipes 60, that is controlled by the main controller cabinet 38. This allows the operator to replace an exact amount of water 46 into the process time and time again, as needed to suit the current job. As above, this function can also be saved for future batches for accurate repeatability of the process.

As shown in FIG. 1, a 24" manway access port/door 62 is used for cleaning and access to an insulated holding tank 64, which is preferably a 55-gallon insulated surge storage reservoir. This permits all water 46 that exits from the separation/collection vessel 52, via valve 78, into holding tank 64 so it can be held in a clean and insulated space in between wash cycles. This is to ensure that the exact same quantitate and water 46 is reused in each successive wash cycle after the first cycle to ensure consistent repetition of the processing. A ¾ ton cold chiller 66 is used to chill food safe glycol that is routed into the glycol jacket 28, as seen in FIGS. 2A, 2B and 3, to chill the main extraction vessel 12 or 12' as well as the chilled water make up tank 48. This enables refrigeration/chill of these tanks to eliminate the need for unreliable ice to be used in this operation in accordance with the present invention. With the assistance of the controller 38, the chiller 66 can be set on a schedule to start and stop at specific times and dates, in similar fashion to a programmable thermostat. Also, storage drawer 68 is used for easy ergonomic access to all cleaning tools and spare parts for this machine and keeps them in an easy to clean and reach space. The inner draw is also removable for periodic cleaning.

Once the hash resin trichomes 42 is extracted using the system and method of the present invention, as mentioned above, it requires further processing before consumption. For example, the collected trichomes 42 will typically be laid out on parchment paper for drying and further processing. For example, the resin trichomes 42 is commonly cut or chopped and then stored so it may dry. The drying process may be carried out in many different ways. Since such drying is so well known in the art, it need not be discussed further herein.

It would be appreciated by those skilled in the art that various changes and modifications can be made to the illustrated embodiments without departing from the spirit of the present invention. All such modifications and changes are intended to be covered by the appended claims.

What is claimed is:

1. A cannabis extraction system, comprising:
   an extraction vessel having an input port and output port; the extraction vessel having an open top end and closed bottom en&
   a mesh washing basket removably located in the extraction vessel; a central post located through a bottom surface of the mesh washing basket at least one agitation paddle attached to the centralpost;
   an internal 8 female spline coupler/drive hub positioned below the mesh washing basket and removably connected to the central post and being configured and arranged for rotating the central post and the at least one agitation paddle attached thereto from below the mesh basket;
   a chilled water tank fluidly connected to the main extraction vessel via the input port; the chiller water tank being configured and arrange to provide water into the extraction vessel;
   a separation/collection tank having an open top end and configured to receive extracted hash resin by gravity from the extraction vessel via the output port of the extraction vessel;
   a pump fluidly connected to the water tank to recirculate water back into the open top end of the extraction vessel; and
   a computerized controller electronically connected to the pump and water tank to controllably deliver cold water to the extraction tank via the open top end thereof.

2. The cannabis extraction system of claim 1, wherein the extraction vessel comprises:
   an inner tank having an inner tank wall and an inner tank bottom;
   an exterior tank having an outer tank wall and an open top end; the inner tank residing within the exterior tank;

a top cover attached to the exterior tank and enclosing the top open end of the exterior tank.

3. The cannabis extraction system of claim 2, wherein the inner tank is a double wall construction defining an inner tank space therein; clean chilled water residing in the inner tank space.

4. The cannabis extraction system of claim 1, further comprising a glycol jacket surrounded by an insulation jacket residing between the inner tank and the exterior tank.

5. The cannabis extraction system of claim 1, wherein the exterior tank is made of stainless steel.

6. The cannabis extraction system of claim 1, further comprising an integrated auger with agitation fins connected thereto attached to the mesh basket.

7. The cannabis extraction system of claim 1, wherein the mesh washing basket includes handles or lifting eyes to facilitate lifting of the mesh washing basket out of the extraction vessel.

8. The cannabis extraction system of claim 1, wherein the separation/collection tank is positioned on a slide out base.

9. The cannabis extraction system of claim 1, further comprising filter media located in the separation/collection tank; the filter media collecting trichomes from fluid exiting the extraction vessel by gravity.

10. The cannabis extraction system of claim 9, wherein the filter media is an array of nested filter bags or filter baskets of varying pore size.

11. The cannabis extraction system of claim 1, wherein the computerized controller logs and tracks amount and temperature of water delivered to the extraction vessel from the chiller water make up tank, and time and agitation power of the rotation of the mesh basket.

12. The cannabis extraction system of claim 1, further comprising at least one vibration device attached to the extraction vessel and/or the separation/collection tank.

* * * * *